(12) United States Patent
Wang et al.

(10) Patent No.: US 10,591,275 B2
(45) Date of Patent: *Mar. 17, 2020

(54) POLARIZATION SENSITIVE OPTICAL COHERENCE TOMOGRAPHY USING MULTIPLE POLARIZATION SENSITIVE SEMICONDUCTOR OPTICAL AMPLIFIERS

(71) Applicant: CASE WESTERN RESERVE UNIVERSITY, Cleveland, OH (US)

(72) Inventors: Hui Wang, Cleveland, OH (US); Andrew Rollins, Highland Heights, OH (US); Xiaoyong Fu, Shaker Heights, OH (US)

(73) Assignee: CASE WESTERN RESERVE UNIVERSITY, Cleveland, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/886,739

(22) Filed: Feb. 1, 2018

(65) Prior Publication Data

US 2018/0156596 A1    Jun. 7, 2018

Related U.S. Application Data

(63) Continuation of application No. 14/512,003, filed on Oct. 10, 2014, now Pat. No. 9,885,557.

(Continued)

(51) Int. Cl.
*G01B 9/02* (2006.01)
*A61B 5/00* (2006.01)

(52) U.S. Cl.
CPC ........ *G01B 9/02011* (2013.01); *A61B 5/0066* (2013.01); *G01B 9/02091* (2013.01);
(Continued)

(58) Field of Classification Search
CPC ............ G01B 9/02011; G01B 9/02091; G01B 2290/70; G01B 2290/60; A61B 5/0066; A61B 5/0084

See application file for complete search history.

(56) References Cited

U.S. PATENT DOCUMENTS 7,929,148 B2    4/2011 Kemp
8,009,297 B2    8/2011 Chan et al.
(Continued)

FOREIGN PATENT DOCUMENTS

WO    2009/140617 A2    11/2009
WO    2010/085618 A1    7/2010

OTHER PUBLICATIONS

Baumann, et al., "Swept source / Fourier domain polarization sensitive optical coherence tomography with a passive polarization delay unit", Apr. 23, 2012/vol. 20, No. 9/Optics Express.

(Continued)

*Primary Examiner* — Hwa Andrew Lee
(74) *Attorney, Agent, or Firm* — Tarolli, Sundheim, Covell & Tummino LLP

(57) ABSTRACT

This disclosure relates to an OCT apparatus configured to generate to electromagnetic (e.g., optical) signals having two different polarization states. Two or more silicon optical amplifiers (SOAs) can be configured to maintain a respective polarization state in an optical input signal provided from a light source (e.g., a broadband light source). The different polarization states can be combined by an optical combiner (e.g., a polarization maintaining fiber coupler) and provided to drive a reference arm and a sample arm implemented in an OCT system.

20 Claims, 6 Drawing Sheets

Related U.S. Application Data

(60) Provisional application No. 61/889,884, filed on Oct. 11, 2013.

(52) U.S. Cl.
CPC ........ *A61B 5/0084* (2013.01); *G01B 2290/60* (2013.01); *G01B 2290/70* (2013.01)

(56) References Cited

U.S. PATENT DOCUMENTS

| | | | |
|---|---|---|---|
| 8,125,648 B2 | 2/2012 | Milner et al. | |
| 8,150,496 B2 | 4/2012 | Tearney et al. | |
| 8,208,996 B2 | 6/2012 | Meyer et al. | |
| 8,908,189 B2 | 12/2014 | Tumlinson | |
| 2004/0064022 A1* | 4/2004 | Korn | A61B 5/0075 600/342 |
| 2007/0109553 A1 | 5/2007 | Feldchtein et al. | |
| 2008/0007734 A1 | 1/2008 | Park et al. | |
| 2008/0252900 A1* | 10/2008 | Hatori | G01N 21/4795 356/482 |
| 2010/0182609 A1 | 7/2010 | Wang et al. | |
| 2011/0109911 A1 | 5/2011 | Podoleanu | |
| 2011/0109914 A1 | 5/2011 | Roth et al. | |
| 2012/0038885 A1 | 2/2012 | Cense et al. | |
| 2013/0100456 A1* | 4/2013 | Yu | H01S 3/0823 356/479 |
| 2015/0138563 A1 | 5/2015 | Wang et al. | |

OTHER PUBLICATIONS

Ju, et al., "Advanced multi-contrast Jones matrix optical coherence tomography for Doppler and polarization sensitive imaging", Aug. 12, 2013 | vol. 21, No. 16.

Bonesi, et al., "High-speed polarization sensitive optical coherence tomography scan engine based on Fourier domain mode locked laser: erratum", Feb. 1, 2013 / vol. 4, No. 2 / Biomedical Optics Express 241.

Oh, et al., "High-speed polarization sensitive optical frequency domain imaging with frequency multiplexing", Jan. 21, 2008 / vol. 16, No. 2 / Optics Express 1096.

Huber, et al., "High speed frequency swept light source for Fourier domain OCT at 20 kHz A-scan rate".

Fleming, et al., "Real-time Imaging of Radiofrequency Cardiac Ablation Using Optical Coherence Tomography", 2008 Optical Society of America.

Fleming, et al., "Monitoring of Radiofrequency Ablation Technology using Optical Coherence Tomography", PhD Long Proposal, Jun. 10, 2008.

* cited by examiner

POLARIZATION SENSITIVE OPTICAL COHERENCE TOMOGRAPHY USING MULTIPLE POLARIZATION SENSITIVE SEMICONDUCTOR OPTICAL AMPLIFIERS

CROSS-REFERENCE TO RELATED APPLICATION

This application claims the benefit of U.S. Provisional Patent Application 61/889,884, filed on Oct. 11, 2013, and entitled POLARIZATION SENSITIVE OPTICAL COHERENCE TOMOGRAPHY, the entirety of which is incorporated by reference herein.

GOVERNMENT FUNDING

This invention was made with government support under Grant No. IIP-0917940 awarded by The National Science Foundation. The United States government has certain rights in the invention.

TECHNICAL FIELD

Background

Optical coherence tomography (OCT) is an optical signal acquisition and processing method. OCT can capture micrometer-resolution, three-dimensional images from within optical scattering media (e.g., biological tissue). Optical coherence tomography is an interferometric technique, typically employing near-infrared light. The use of relatively long wavelength light allows it to penetrate into the scattering medium. Depending on the properties of the light, OCT can achieve sub-micron resolution.

Most conventional OCT systems use non-polarization-maintaining (PM) single-mode fiber interconnections and operate by measuring the depth-resolved reflectivity profile of backscattered light. Such non-PM OCT systems are generally inexpensive, allow for easy alignment and handling, and enable flexible sample arm designs which are important for in vivo measurements, such as surgical and endoscopic applications. Polarization-sensitive OCT (PS-OCT) systems have been developed to detect the polarization states reflected from the different depths of tissue by controlling the polarization state of light incident upon the sample.

SUMMARY

This disclosure relates to polarization sensitive optical coherence tomography.

As one example, An optical coherence tomography (OCT) apparatus includes a light source configured to provide broadband light. A first polarization sensitive semiconductor optical amplifier (PS-SOA) can receive a portion of the broadband light and to output a first polarized optical signal having a first polarization state. A second PS-SOA can receive another portion of the broadband light and to output a second polarized optical signal having a second polarization state, the first and second polarization states being different.

As another example, a method of implementing polarization sensitive optical coherence tomography, can include providing a broadband light signal and amplifying a first polarization state for a first portion of the broadband light using a first polarization sensitive semiconductor optical amplifier to output a first polarized optical signal having the first polarization state. The method can also include amplifying a second polarization state for a second portion of the broadband light using another polarization sensitive optical amplifier to output a second polarized optical signal having a second polarization state, the first and second polarization states being different.

As yet another example, a system for implementing polarization sensitive optical coherence tomography can include a light apparatus. The light apparatus can include a light source configured to provide broadband light and a first polarization sensitive semiconductor optical amplifier (PS-SOA) to receive a portion of the broadband light and to output a first polarized optical signal having a first polarization state. The light apparatus also includes a second PS-SOA to receive another portion of the broadband light and to output a second polarized optical signal having a second polarization state, the first and second polarization states being different. The system can also include an optical combiner to adapted to combine the first and second polarized optical signals to provide an aggregate polarized optical signal. The system can also include an optical splitter configured to receive the aggregate polarized optical signal and provide a portion of the aggregate polarized optical signal to a reference arm and another portion of the aggregate polarized optical signal to a sample arm. The system can also include an optical detector to receive signals from each of the reference arm and the sample arm and to provide at least one detector signal based on reflected signals from the reference arm and the sample arm. The system can also include a processor programmed to calculate at least one optical property for a sample associated with the sample arm based on the at least one detector signal.

DETAILED DESCRIPTION

This disclosure relates to polarization sensitive optical coherence tomography (PS-OCT). A system includes an OCT apparatus configured to generate to electromagnetic (e.g., optical) signals having two different polarization states. In one example, the light source itself can be configured to generate the different polarization states directly, which can be provided to respective polarization sensitive semi-conductor optical amplifiers (PS-SOA). Each PS-SOA is configured to maintain a particular polarization state.

In another example, the light source can provide a single optical signal that can be split to provide respective portions of the optical signal to respective PS-SOAs, which are configured to enforce predetermined different polarization states. As another example, the light source can be implemented to provide two different outputs, each of which can be converted to predetermined polarization states via two or more PS-SOAs or split into two different polarization states through a polarization sensitive beam splitter. In some examples, the light provided to each SOA can be polarized with a polarization controller. In other examples, the polarization state can be the same that is provided to each PS-SOA, and the PS-SOAs can be controlled to generate desired different polarization states. The different polarization states can be polarization states offset by a predetermined angle (e.g., about 90 degrees, 45 degrees or any other different polarization states having a known relationship). In such examples, the different polarization states can be combined by an optical combiner (e.g., a polarization maintaining fiber coupler) to drive a reference arm and a sample arm implemented in the OCT system. Additionally, by implementing the PS-SOAs, the different polarization states can be maintained with the predetermined relationship in the absence of a polarization modulator in the OCT light apparatus.

Figure 1:
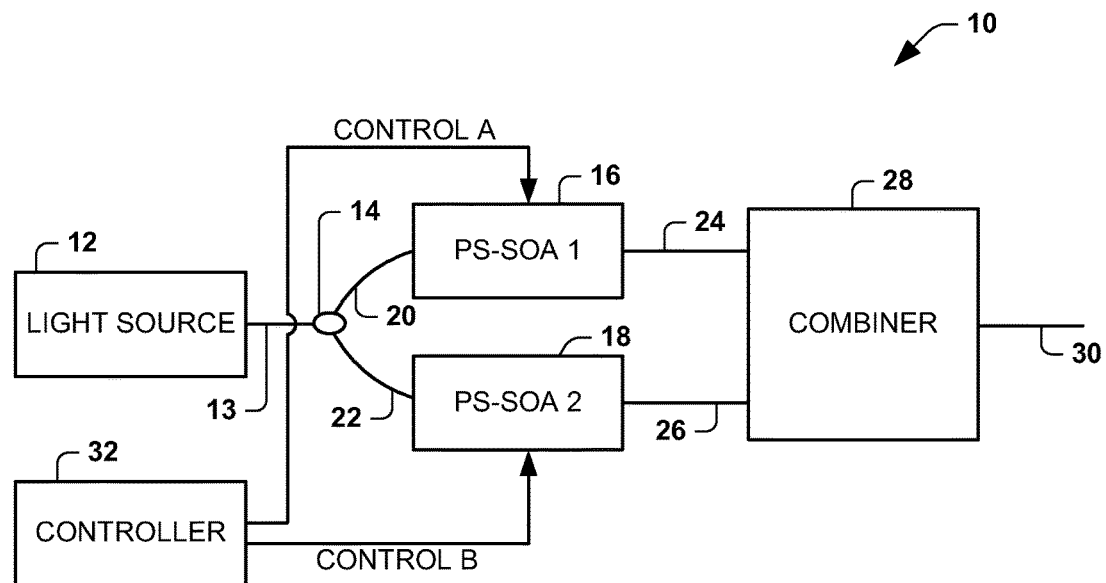
FIG. 1 depicts an example of a polarization sensitive OCT light system.

FIG. 1 is an example of an OCT light apparatus 10. The apparatus 10 includes a light source 12 that is configured to generate electromagnetic radiation, such as light centered at a predetermined wavelength. For example, the light source 12 can be a laser configured to generate an optical signal that is provided via a wave guide (e.g., an optical fiber or any other wave guide) to a splitter 14. For example, the splitter 14 can be fiber optic beam splitter having a single input port 13 and a pair of output ports 20 and 22, such that the splitter is configured to split the optical signal into two respective portions (e.g., substantially equal portions) that are provided to PS-SOA 16 and PS-SOA 18. Depending on the type of waveguide for propagating the light from the light source 12, in some examples, the splitter 14 can be implemented as a polarizing beam splitter (e.g., Glan-Foucault prism) configured to generate two different output signals having different polarization states. In the example of an optical fiber waveguide, the splitter could be implemented as a fiber coupler that generates the respective output signals.

Each PS-SOA 16 and 18 is configured to enforce a particular polarization state that is provided in a respective output signal 24 and 26, respectfully. Each PS-SOA 16 and 18 provides an output optical signal having a respective polarization state to a combiner 28 that is configured to optically combine the different polarization states into an aggregate output optical signal 30. Such aggregate signal 30 can be provided as an input to the OCT system for driving respective reference and sample arms (see, e.g., FIGS. 8 and 9).

The PS-SOAs 16 and 18 can be implemented as optical amplifiers based on a semiconductor gain medium. The input signal light from the splitter 14 is usually sent through a semiconductor waveguide within each PS-SOA 16 and 18, which includes an active region that is pumped by electrical current signals control A and B. The injection current creates a certain carrier density in the conduction band, allowing for optical transitions from the conduction band to the valence band. The PS-SOAs 16 and 18 are configured to be polarization sensitive, namely that the amplification resulting from the current injection is applied discriminately to a corresponding polarization state. For example, each of the PS-SOAs 16 and 18 can be operated to selectively amplify different polarization states, such that the outputs 24 and 26 can be amplified optical signal components having predetermined different respective polarization states depending on the polarization state at which the amplification is applied.

In the example of FIG. 1, a controller 32 is configured to provide respective control signals, indicated at Control A and Control B, to the respective PS-SOAs 16 and 18. Each control signal, for example, can be provided to establish a desired difference between the respective polarization states in the respective output signals provided at 24 and 26. Additionally, the control signals can be applied such that the output signals also exhibit a desired phase difference, namely, to be out of phase to facilitate interferometric measurements. For example, the control signals can be pulse width modulated signals (e.g., having a 50% duty cycle or less) that have a phase difference to establish desired polarization states (e.g., 180 degrees out of phase from each other).

Figure 2:
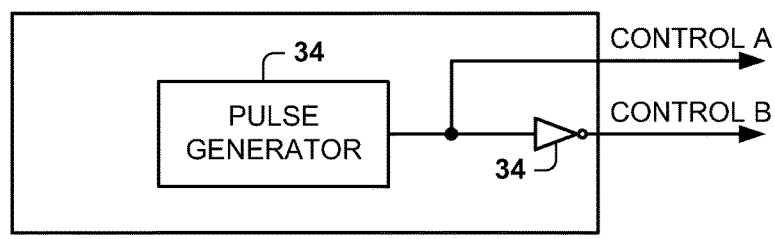
FIG. 2 depicts an example of a controller that can be utilized in the system of FIG. 1.

An example of the controller used to generate the control A and Control B signals is illustrated in FIG. 2. In the example of FIG. 2, the controller 32 is demonstrated as including a pulse generator 34 that is configured to provide a periodic output signal corresponding to control A. The signal control A has a duty cycle that is 50% or less. The signal is provided to an inverter 36 that in turn provides control B signal that is 180 degrees out of phase from control A. In this way, control signals A and B can be asserted mutually exclusively and utilized to operate PS-SOA1 and PS-SOA2 in a periodic out of phase operation. Additionally, for providing the respective different polarization states, such as can be orthogonal linear polarization or other relative polarization states. While, in this example, orthogonal polarization states are implemented by the controller 32, PS-SOA 16 and 18, it is to be understood that any desired polarization state can be generated via configuring various combinations of these components.

Figure 3:
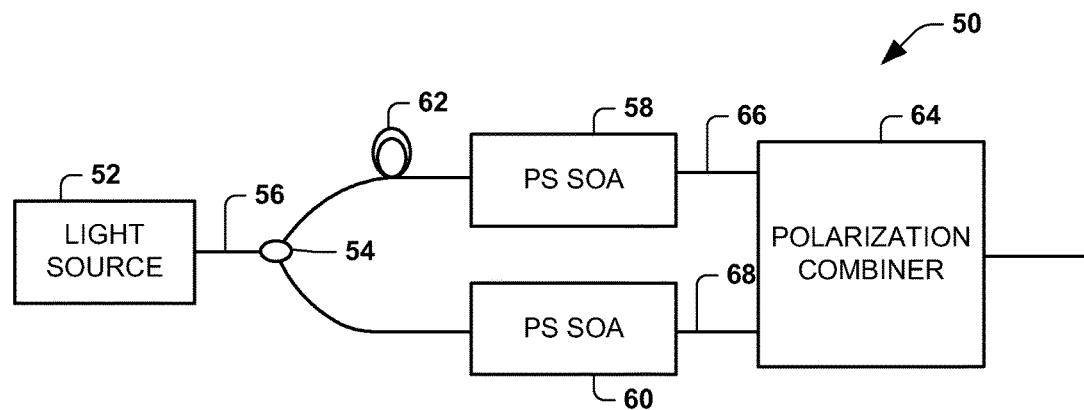
FIG. 3 depicts an example of another polarization sensitive OCT light system.
Figure 7:
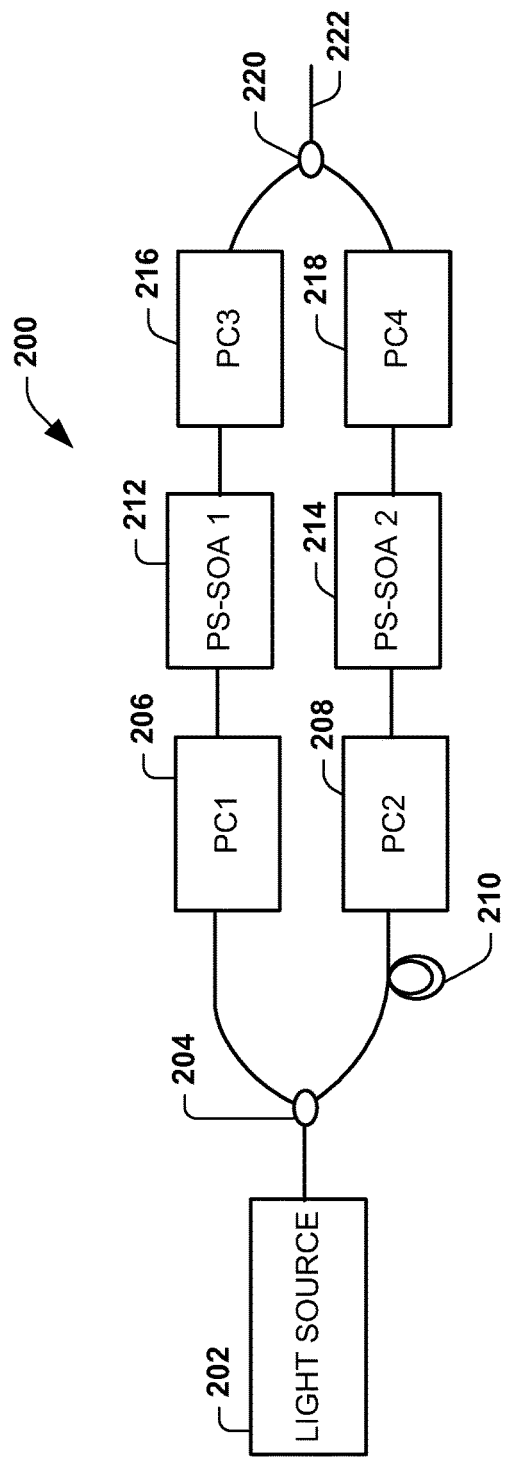
FIG. 7 depicts an example of still another polarization sensitive OCT light system.

FIG. 3 depicts another example of an OCT light apparatus 50 that can be utilized to provide different polarization states for use in a PS OCT system (e.g., the system of FIG. 7). In the example of FIG. 3, the apparatus 50 includes a light source 52 that is configured to provide broadband light to a splitter 54 via a corresponding waveguide 56. For example, the light source 52 can be implemented as a swept source laser that provides an output to an optical fiber (corresponding to the waveguide 56) connected between the splitter 54.

The splitter 54 can provide a portion of the broadband light to a first PS-SOA 58 via a corresponding waveguide, and another portion of the light to PS-SOA2 60. For example, the splitter 54 can be implemented as an optical fiber coupler that divides (e.g., in a balanced manner) the light from the light source 52 to each of the PS-SOAs 58 and 60, such as via optical fibers or other optical wave guides. In order to implement a phase shift between the respective different polarization states, an optical delay line 62 can be provided between the optical splitter 54 and one of the PS-SOAs 58. The delay line 62 can thus implement a desired phase shift between the respective portions of the broad band light provided by the splitter 54, such that the respective signals to the PS-SOAs 58 and 60 can be out of phase with each other to facilitate corresponding OCT analysis.

Each of the PS-SOAs 58 and 60 is configured to amplify a different polarization state in the signal portions, such as can be orthogonal polarization states or other different relative amounts of polarization. Additionally or alternatively, output fibers 66 and 68 can be twisted to achieve the desired polarization states. Thus, different polarization states are provided from each of the PS-SOAs 58 and 60 and have different phase due to the phase shift provided by the delay line 62.

In some examples, the outputs of 58 and 60 can be further manipulated by adding polarization controllers (PCs—not shown) on the output fibers 66 and 68 between the PS-SOAs and polarization combiner 64. The PCs can be used to help optimize the spectrum and balance the power from the PS-SOAs 58 and 60. The PC can be designed to transform an arbitrary polarization into a predetermined fixed polarization, such as by manual configuration or by employing automatic feedback. The polarization controller can be implemented using free space optics or an all-fiber solution, which can vary depending on application requirements, for example. Such PC can be used in all configurations disclosed herein (e.g., also in FIGS. 1, and 3-9) for this purpose.

Each PS-SOA 58 and 60 can be coupled to drive a polarization combiner 64 via connected optical fibers corresponding to the outputs 66 and 68 between the respective PS-SOA and the combiner 64. Corresponding aggregate optical signal carrying the different polarization states and different phase predetermined phase relationships thus can be provided for use in performing OCT as disclosed herein (see, e.g., FIGS. 8 and 9).

Figure 4:
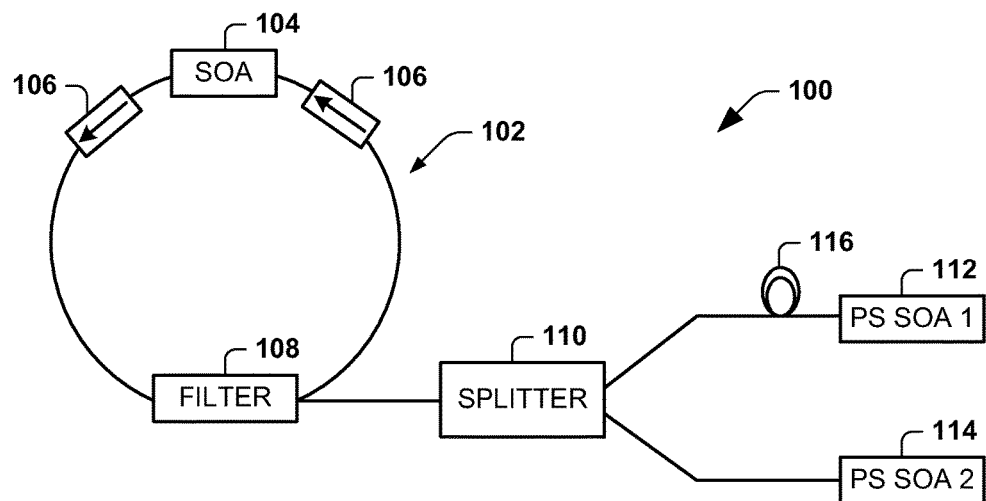
FIG. 4 depicts an example of another polarization sensitive OCT light system.

FIG. 4 depicts an example of another OCT light apparatus 100 that can generate different polarization states for use in a PS-OCT system. The apparatus 100 includes a light source that is implemented as an optical ring resonator 102, such as can be a tunable laser for providing an output having a desired polarization state. In the example of FIG. 4, the OCT light apparatus 100 includes an SOA 104 configured as a gain medium to optically amplify resonating optical signals propagating in the resonator 102. The ring resonator 102 also includes optical isolators 106 coupled to both the input and output of the SOA 104 for maintaining the directionality of the light through the ring resonator 102. The ring resonator 102 can also include one or more filters 108 optically coupled to the respective isolators 106 and configured to provide a filtered amplified broadband optical output to a splitter 110 with a particular polarization state. That is, the filter 108 can be configured to transmit part of the circulating intracavity optical power to generate a useful output having one or more polarization states. The output signal can be separated into different portions by the splitter (e.g., a fiber coupler) 110 and provided to respective PS-SOA1 and PS-SOA2 demonstrated at 112 and 114.

Each of the different portions of the output from the filter 108 can include the one or more polarization states. For example, the splitter can be coupled to each PS-SOA 112 and 114 via an optical fiber such as a PM optical fiber. In one of the paths, between the splitter 110 and the PS-SOA 112 a delay line 116 can be provided to implement a desired phase shift in the optical signal such that each of the signals provided to PS-SOA1 and PS-SOA2 have different phase shifts (e.g., the signals are asserted out of phase) to facilitate OCT analysis. Each PS-SOA 112 and 114 thus be configured to amplify a particular different polarization state contained in the respective portions of the output signals. In this way, each PS-SOA 112 and 114 can generate output signals of desired amplitude and different polarization states (e.g., orthogonal linear polarization states) that are out of phase relative to each other. The respective outputs from the PS-SOAs 112 and 114 can be combined and provided to a PS-OCT system such as disclosed herein (see, e.g., FIGS. 8 and 9).

Figure 5:
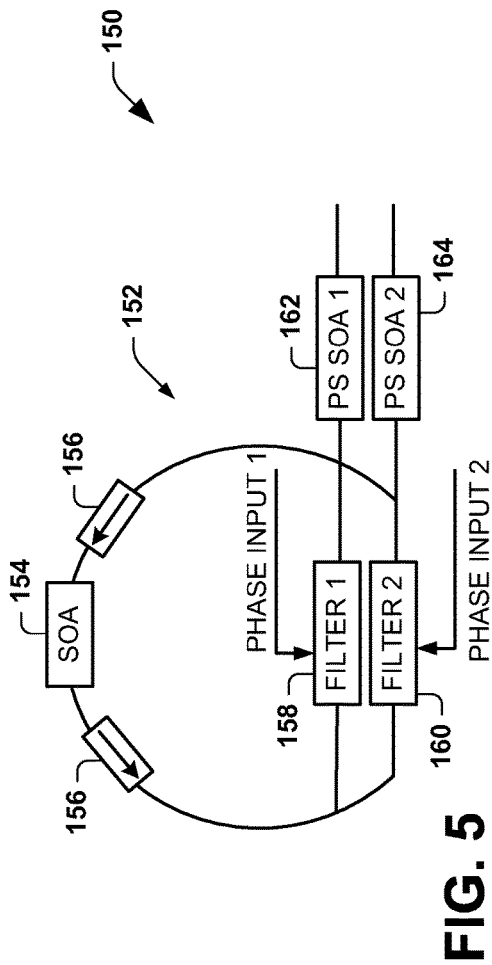
FIG. 5 depicts an example of another polarization sensitive OCT light system.

FIG. 5 illustrates another example of a light source apparatus 150 that can be utilized for generating optical signals having different predetermined polarization states. In the example of FIG. 5, the apparatus 150 includes a light source implemented as an optical ring resonator 152, which is similar to the example in FIG. 4. Briefly stated, the optical ring resonator includes a SOA 154 as a gain medium and optical isolators 156 coupled to the input and output of the SOA to amplify the resonating signal.

In the example of FIG. 5 a pair of intracavity filters 158 and 160 are coupled to the resonator (e.g., as fiber couplers) for providing respective optical outputs. Each of the intracavity filters 158 and 160 can be controlled by phase input signals, such as can be 180 degrees out of phase with respect to each other. For example, each of the filters 158 and 160 can be driven with sinusoidal electrical waveforms having 180 degree phase difference. In this way, the respective polarized signals are provided with a desired phase shift to respective PS-SOAS 162 and 164. Each of the PS-SOAs 162 and 164 can be configured to amplify a different predetermined polarization state in the signals provided by the filters 158 and 160, respectively, such that the outputs provided by each PS-SOA have different predetermined polarization states and comparable amplitudes. The different polarized signals that are out of phase can in turn be provided to a combiner for providing an aggregate signal having at least two polarization states that are out of phase, such as disclosed herein (see, e.g., FIGS. 8 and 9).

Figure 6:
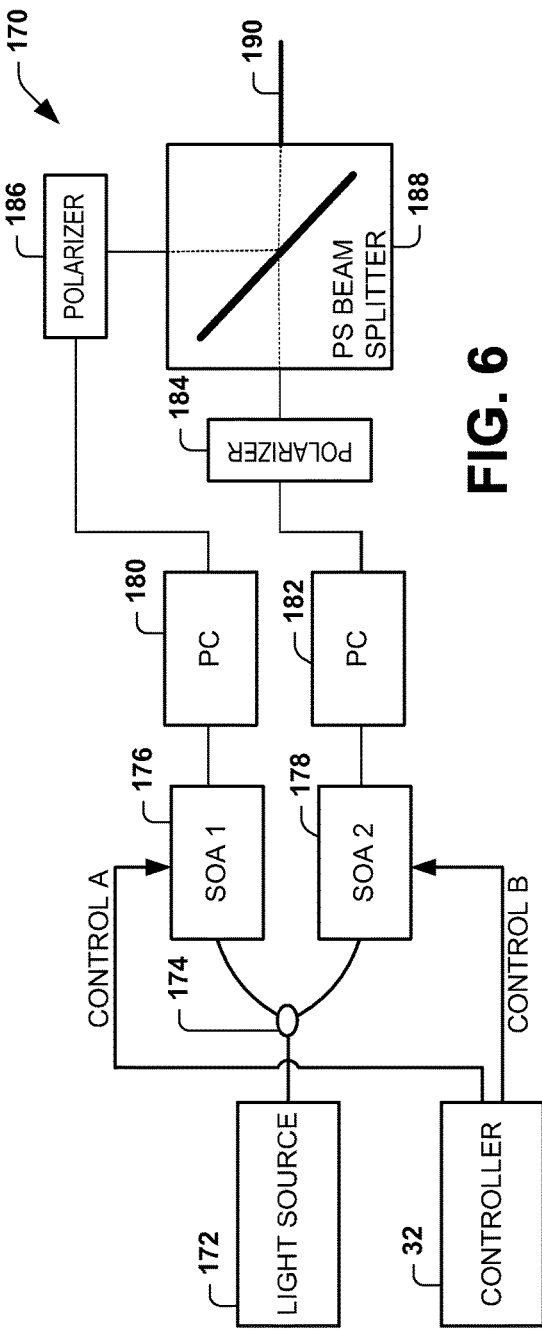
FIG. 6 depicts an example of yet another polarization sensitive OCT light system.
Figure 8:
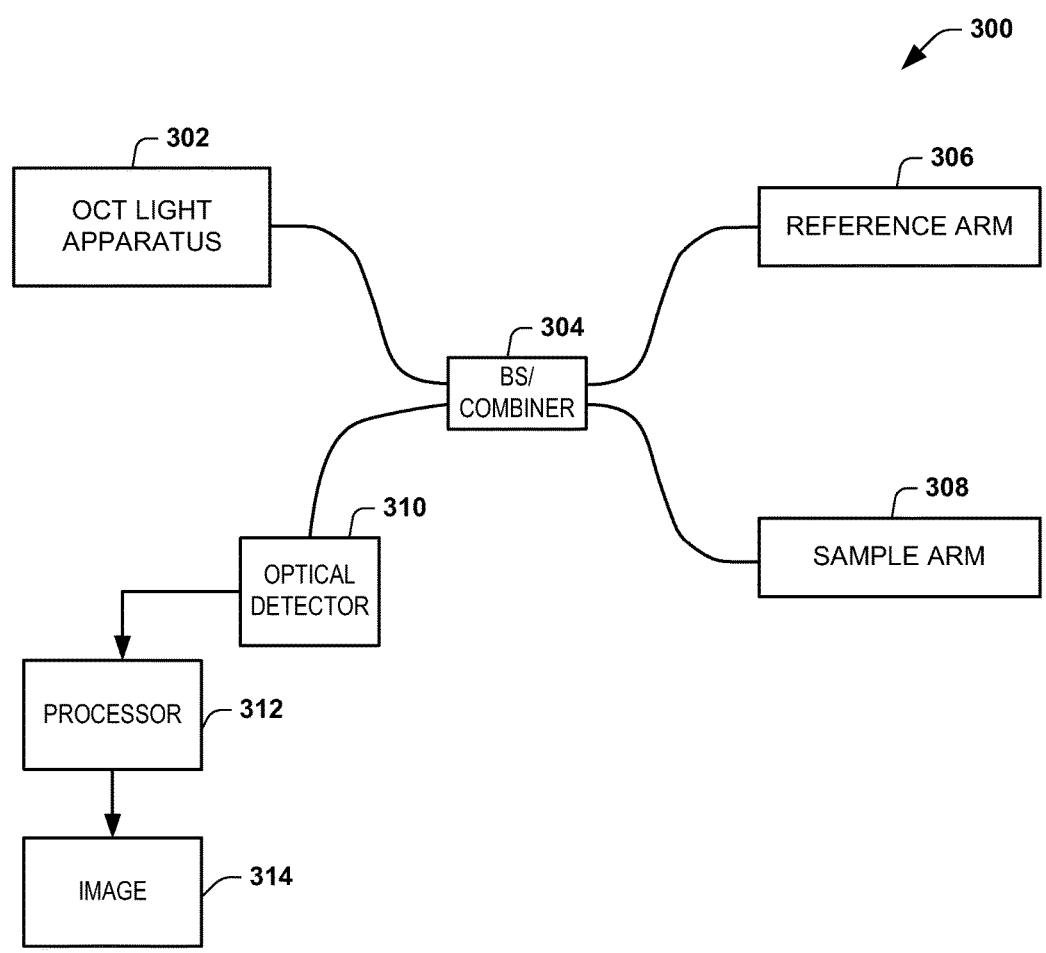
FIG. 8 depicts an example of an OCT system implementing a polarization sensitive OCT light system.
Figure 9:
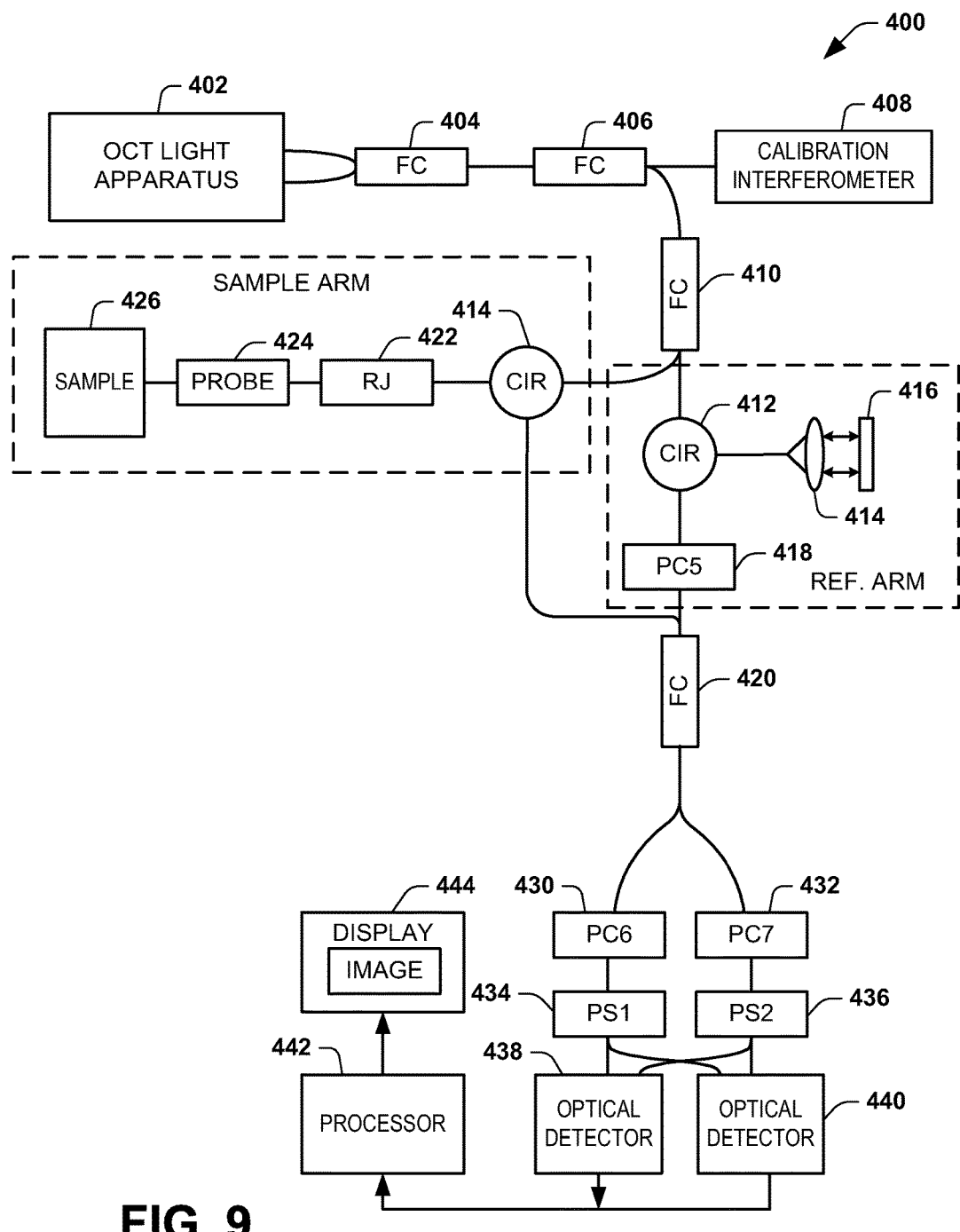
FIG. 9 depicts another example of an OCT system implementing a polarization sensitive OCT light system.

FIG. 6 depicts yet another example of an OCT light apparatus 170 that can be utilized to provide different polarization states for use in a PS OCT system (e.g., the system of FIGS. 8 and 9). The apparatus 170 is similar to the apparatus 10 of FIG. 1. Briefly stated, the apparatus includes one or more light sources 172 to generate electromagnetic radiation, such as light having a wavelength centered at a predetermined wavelength. The light source 172 can provide one or more optical signals to an optical splitter 174. The splitter 174 can be configured to split the optical signal from the source 172 into respective portions that are provided to SOA 176 and SOA 178. In contrast to FIG. 1, the SOAs 176 and 178 in this example are normal SOAs and not polarization sensitive SOAs. Thus, they amplify the optical input signals without enforcing (by amplification) a particular polarization state. Each SOA 176 and 178 provides a respective signal to polarization controllers (PCs) 180 and 182. Each PC 180 and 182 can optimize the spectrum as well as balance the power from the SOAs 176 and 178. Each of the PCs 180 and 182 can provide respective signals to a polarizer 184 and 186. Each polarizer can be configured to enforce a particular polarization state that is provided in a respective output signal. Each PS polarizer 184 and 186 thus provides a respective signal with corresponding different polarization state to a combiner 188 that is configured to optically combine the different polarization states into an aggregate output optical signal 190. As an example, the combiner 188 can be implemented as a polarization sensitive beam splitter that is configured to implement both the polarization of the respective signals as well as to combine the polarized signals and provided the combined output optical signals 190. Thus, a polarizer can be utilized to generate different polarization states and/or use a polarization beam splitter to both polarize and combine the respective signals to provide the aggregate signal. Such aggregate signal 190 can be provided as an input to the OCT system for driving respective reference and sample arms (e.g., see FIGS. 8 and 9).

In the examples of FIGS. 1 and 3-5, for purposes of simplicity of explanation, the apparatuses did not include explicitly demonstrate a PC. However, each of the examples could include PCs similar to the example of FIG. 6. For example, in FIG. 1, a PC could be implemented between the splitter 14 and each PS-SOA 16 and 18. In FIG. 3, a PC could be implemented between the splitter 54 and each PS-SOA 59 and 60. In FIG. 4, a PC could be implemented between the splitter 110 and each PS-SOA 112 and 114. In FIG. 5, a PC could be implemented between each filter 158 and 160 and each respective PS-SOA 162 and 164.

FIG. 7 depicts an example of still another embodiment of an OCT light apparatus 200. The apparatus includes a light source 202 to generate electromagnetic radiation, such as light having a wavelength centered at a predetermined wavelength. For example, the light source 202 can be implemented as a Fourier-domain mode-locked (FDML) laser having approximately 50% duty cycle, a center wavelength of about 1310 nm, a bandwidth of about 100 nm, and a sweep frequency of about 58.5 kHz. Other type of light sources could be utilized. The light source 202 can provide one or more optical signals to an optical splitter 204. The splitter 174 can be configured to split the optical signal from the source 172 into respective substantially equal portions that are provided to respective PCs 206 and 208 (demonstrated as PC1 and PC2). The optical signal provided to one of the PCs 208 can be phase shifted with respect to the signal provided to the other PC 206. For instance, a delay line (e.g., a coil of fiber) 210 can implement a predetermined delay, such as about half of the period of the optical pulse. Thus, the signals provided to the PCs 206 and 208 are out of phase with respect to each other. The output of PCs 206 and 208 are provided to respective PS-SOAs 212 and 214 that amplify the respective optical signals to enforce different predetermined polarization states. The PCs are placed before the booster SOAs to help optimize the laser amplification and the PS-SOAs produce alternating laser sweeps.

In this example, the PS-SOAs 212 and 214 can operate in saturation to force the output light from the light source into linearly polarized states. An additional PC 216 and 218 (PC3 and PC4) is placed after each of the booster SOAs to manipulate the alternating laser sweeps into two different linear polarization states, such as at 0 degrees and 45 degrees (90 degrees from each other on the Poincare sphere). By maintaining polarization states that are about 45 degrees apart can help ensure non-alignment between fast and slow axes, such as to ensure information can be obtained from a sample arm (see, e.g., FIGS. 8 and 9).

A combiner 220 receives the output signals from the PCs 216 and 218 to recombine the amplified light, which is differently linearly polarized and out of phase light, from the PS-SOAs. The combiner 220 can be a fiber coupler to provide the aggregate light via an output optical fiber 222. The passive multiplexing of alternating polarization states using a buffer fiber spool does not require synchronization of any active component with A-scan data acquisition. Thus, the example of FIG. 7 provides a simple approach that can implement an all-fiber optic PSOCT with an FDML laser, for example.

FIG. 8 depicts an example of an OCT system 300 that can be utilized for generating an OCT image of a sample (e.g., a biological sample). The system 300 includes an OCT light apparatus 302 configured to provide an optical signal that includes two or more different polarization states which are out of phase with respect to each other. The OCT light apparatus 302 can be implemented according to any of the examples disclosed herein with respect to FIGS. 1-7. While in each of the examples of FIGS. 1-7, two PS-SOAs are demonstrated as providing the different polarization states, there can be any number N of PS-SOAs (where N is a positive integer greater than or equal to 2) to provide different respective polarization states. As mentioned, the OCT light apparatus 302 can be a swept source laser in which the light source encodes different spectral components temporally over a predetermined frequency range.

The OCT light apparatus 302 can provide the combined polarized and out of phase optical signals to a beam splitter/combiner 304. For example, a PM optical fiber or other PM wave guide can provide the optical signal from the light apparatus 302 to the splitter/combiner 304. The splitter/combiner 304 can in turn provide a portion of the signal to a reference arm 306 and another portion of the signal to a corresponding sample arm 308. The reference arm 306 can include a reflector (e.g., or a mirror) or other structure (e.g., a fiber delay loop) configured to return a reference optical signal back to the beam splitter/combiner 304. Another portion of the signal from the OCT light apparatus 302 can be provided to the sample arm 308 via the beam/combiner 304. The sample arm 308 can be configured to provide the corresponding sample signal to illuminate a sample, such as a biological sample, which may be in vivo or on a surface of a subject. As disclosed herein, the sample signal to illuminate the sample thus includes out of phase optical signals and different polarization states. Light reflected from the sample can be returned from the sample arm 308 to the combiner 304. The combiner 304 thus can combine light from the reference arm and the sample arm and provide the combined optical signal to an optical detector 310.

The optical detector 310 can be a charge coupled device, a photodetector or other form optical sensing device. The optical detector 310 can provide an electrical output signal to a processor representing the detected optical signals from the reference arm 306 and the sample arm 308.

The processor 312 can perform interferometry and calculations on the detector signal and compute optical properties of the sample that is illuminated, such as including diattenuation, birefringence and/or fast axis. Additionally or alternatively, the processor can also compute other optical properties such as total reflective power, B polarization, net retardance or net extinction ratio based on processing of the signals received from the sample arm and reference arm. The processor can utilize the computation to in turn generate a corresponding OCT image that can be presented on a display and/or stored in memory.

FIG. 9 depicts an example of another PS OCT system 400, demonstrating examples embodiments of the reference arm 306 and sample arm 308. For example, the system 400 can be implemented to provide a fiber-optic catheter-based PSOCT system. The system 400 includes an OCT light apparatus to produce two or more out of phase light signals having predetermined polarization states. The light apparatus can be any of the embodiments disclosed herein (FIGS. 1-7). As one particular example, the OCT light source is the light source demonstrated in FIG. 7. The optical signals are combined by a fiber coupler 404 or other combiner.

The light can then be split by an optical fiber coupler 406 into respective different portions. A relatively smaller portion of the split light (e.g., about 10%) can be used for a calibration interferometer 408 to provide the signal used to linearize the spectral interferogram. The other, larger portion (e.g., about 90%) is connected to an unbalanced OCT interferometer, such as can be implemented as a Mazh-Zehnder OCT interferometer. For example, another fiber coupler 410 can be employed to split the light into respective portions (e.g., about 90% and about 10%) to provide the respective portions to a sample arm (e.g., sample arm 308)

and a reference arm (e.g., reference arm 306), such as via circulators 412 and 414 in the respective reference and sample arms.

For example, in reference arm 306, the circulator 412 can drive the reference signal through a lens 414 to a mirror 416, which reflects the light through the mirror and back to the circulator. The circulator 412 can also provide the combined circulated light reference signal to a polarization controller (PC5) 418. The polarization controller enforces a polarization state for the reference arm and provides a polarized output to an output fiber coupler 420.

In the sample arm, the circulator provides the sample light signal from the fiber coupler 410 to a probe apparatus 424 through a rotating joint 422, for example. The probe emits the sample light having the desired polarization states and respective phases on a sample for interrogation. The probe also receives reflected sampled light encoding birefringence characteristics according to the properties of the sample. The sampled light is returned to the circulator 414 and provided to the fiber coupler 420. The fiber coupler 420 thus provides sample and reference optical signals to a detection unit.

In the example of FIG. 9, the detection unit includes respective reference and sample channels, including an arrangement of polarization controllers 430, 432, polarizing beam splitters (PS1 and PS2) 434 and 436, and balanced optical detectors 438 and 440. The outputs from the optical detectors 438 and 440 can be processed and evaluated by a processor 442 to compute values representing detected optical properties of the sample. For example, the processor can compute two or more of total reflected power, diattenuation, depolarization, birefringence, net retardance and net fast axis or extinction ratio. The computed optical properties can be provided to a display 444 to provide a graphical output image corresponding to the sample. For example, the processor 442 can utilize Stokes vectors and Mueller calculus to calculate the phase retardation map of the birefringent samples. The PSOCT system 400 can configured to acquire OCT images at frame rate and resolution (e.g., about 50 frames per second or faster with about 1000 A-lines or more per frame).

What have been described above are examples and embodiments of the invention. It is, of course, not possible to describe every conceivable combination of components or methodologies for purposes of describing the invention, but one of ordinary skill in the art will recognize that many further combinations and permutations of the present invention are possible. Accordingly, the invention is intended to embrace all such alterations, modifications and variations that fall within the scope of the appended claims. In the claims, unless otherwise indicated, the article "a" is to refer to "one or more than one."

What is claimed is:

1. An optical coherence tomography (OCT) apparatus, comprising:
    a light source configured to provide broadband light;
    a first polarization sensitive semiconductor optical amplifier (PS-SOA) to receive a portion of the broadband light and to output a first polarized optical signal having a first polarization state; and
    a second PS-SOA to receive another portion of the broadband light and to output a second polarized optical signal having a second polarization state, the first and second polarization states being different.

2. The apparatus of claim 1, further comprising a splitter coupled between the light source and each of the first PS-SOA and the second PS-SOA, the splitter providing respective portions of the broadband light to each of the first PS-SOA and the second PS-SOA.

3. The apparatus of claim 2, wherein the light source further comprises an intracavity filter configured to tune the broadband light and provide the broadband light to the splitter with a corresponding polarization state.

4. The apparatus of claim 1, further comprising a delay line between the light source and at least one of the PS-SOAs configured to delay a respective portion of the broadband light provided to one of the first PS-SOA and the second PS-SOA relative to the broadband light provided to the other of the first PS-SOA and the second PS-SOA, such that the broadband light provided to the first and second PSSOAs have a predetermined relative phase shift.

5. The apparatus of claim 4, further comprising a combiner configured to combine the first polarized optical signal and the second polarized optical signal to provide an aggregate polarized optical signal having the first and second polarization states and the relative phase shift.

6. An OCT system comprising:
    the apparatus of claim 5;
    an optical beam splitter/combiner configured to receive the aggregate polarized optical signal and provide a portion of the aggregate polarized optical signal to a reference arm and another portion of the aggregate polarized optical signal to a sample arm;
    an optical detector to receive signals from each of the reference arm and the sample arm and to provide a detector signal based on reflected signals in each of the reference arm and the sample arm; and
    a processor programmed to calculate at least one optical property for a sample associated with the sample arm based on the detector signal.

7. The OCT system of claim 6, wherein the at least one optical property includes at least two of total reflected power, diattenuation, depolarization, birefringence, net retardance and net fast axis or extinction ratio.

8. The apparatus of claim 1, further comprising a controller coupled to control each of the first PS-SOA and the second PS-SOA as to generate the first and second polarized optical signals with the different polarization states and out phase with respect to one another.

9. The apparatus of claim 1, wherein the light source further comprises:
    a first intracavity filter configured to tune the broadband light and provide the broadband light having the first polarization state to the first PS-SOA; and
    a second intracavity filter configured to tune the broadband light and provide the broadband light having the second polarization state to the second PSSOA.

10. The apparatus of claim 9, further comprising:
    a first phase modulator configured to drive the first intracavity filter to control the first polarization state of the broadband light; and
    a second phase modulator configured to drive the second intracavity filter to control the second polarization state of the broadband light.

11. The apparatus of claim 1, wherein the light source comprises a swept laser source that includes an optical ring cavity that includes at least one optical isolator to control a direction of light propagation in the optical ring cavity.

12. The apparatus of claim 1, wherein the first and second polarization states are maintained with a predetermined relationship in the absence of a polarization modulator.

13. The apparatus of claim 1, wherein the first and second polarization states exhibit linear polarization that are less than or equal to about 90 degrees apart.

14. The apparatus of claim 1, further comprising a respective polarization controller configured between the light source and each PS-SOA to help optimize a signal spectrum and balance power that is provided to each PS-SOA.

15. The apparatus of claim 14, further comprising another polarization controller configured between each PS-SOA and a combiner.

16. A method of implementing polarization sensitive optical coherence tomography, comprising:
   providing a broadband light signal;
   amplifying a first polarization state for a first portion of the broadband light using a first polarization sensitive semiconductor optical amplifier to output a first polarized optical signal having the first polarization state; and
   amplifying a second polarization state for a second portion of the broadband light using another polarization sensitive optical amplifier to output a second polarized optical signal having a second polarization state, the first and second polarization states being different.

17. The method of claim 16, further comprising:
   controlling polarization of the first portion of the broadband light signal that is provided to the first polarization sensitive semiconductor optical amplifier; and
   controlling polarization of the second portion of the broadband light signal that is provided to the another polarization sensitive optical amplifier.

18. The method of claim 17, further comprising:
   controlling polarization of the first polarized optical signal having the first polarization state; and
   controlling polarization of the second polarized optical signal having the second polarization state.

19. A system for implementing polarization sensitive optical coherence tomography, comprising:
   a light apparatus comprising:
   a light source configured to provide broadband light;
   a first polarization sensitive semiconductor optical amplifier (PSSOA) to receive a portion of the broadband light and to output a first polarized optical signal having a first polarization state; and
   a second PS-SOA to receive another portion of the broadband light and to output a second polarized optical signal having a second polarization state, the first and second polarization states being different;
   an optical combiner to combine the first and second polarized optical signals to provide an aggregate polarized optical signal;
   an optical splitter configured to receive the aggregate polarized optical signal and provide a portion of the aggregate polarized optical signal to a reference arm and another portion of the aggregate polarized optical signal to a sample arm;
   an optical detector to receive signals from each of the reference arm and the sample arm and to provide at least one detector signal based on reflected signals from the reference arm and the sample arm; and
   a processor programmed to calculate at least one optical property for a sample associated with the sample arm based on the at least one detector signal.

20. The system of claim 19, wherein the light apparatus further comprises:
   a delay line between the light source and one of the first and second PSSOAs; and
   at least one polarization controller between the light source and each of the first and second PS-SOAs.

* * * * *